United States Patent [19]

Phipps et al.

[11] Patent Number: 5,188,122
[45] Date of Patent: Feb. 23, 1993

[54] ELECTROMAGNETIC ENERGY GENERATION METHOD

[75] Inventors: Jeffrey H. Phipps, Broughton Ashley; Stanley B. Field, London, both of United Kingdom

[73] Assignee: Rocket of London Limited, Watford, England

[21] Appl. No.: 540,614

[22] Filed: Jun. 20, 1990

[30] Foreign Application Priority Data

Jun. 20, 1989 [GB] United Kingdom ............... 8914118.8
Jun. 29, 1989 [GB] United Kingdom ............... 8914933.0
Dec. 15, 1989 [GB] United Kingdom ............... 8928347.7

[51] Int. Cl.$^5$ ............................................. A61N 5/00
[52] U.S. Cl. ................................... 128/788; 128/401; 128/804; 606/33
[58] Field of Search ............... 128/788, 789, 804, 802, 128/643, 401; 606/41, 49, 33

[56] References Cited

U.S. PATENT DOCUMENTS

| 1,620,929 | 3/1927 | Wallerich | 128/788 |
|---|---|---|---|
| 1,827,306 | 10/1931 | Chapman et al. | 128/788 |
| 3,645,265 | 2/1972 | Majzlin | 128/788 X |
| 3,840,016 | 10/1974 | Lindemann | 128/788 X |
| 4,057,063 | 11/1977 | Gieles et al. | 128/788 X |
| 4,676,258 | 6/1987 | Inokuchi et al. | 128/804 |
| 4,865,047 | 9/1989 | Chou et al. | 128/788 X |
| 4,949,718 | 8/1990 | Neuwirth et al. | 128/401 |
| 4,960,133 | 10/1990 | Hewson et al. | 128/643 X |
| 4,961,435 | 10/1990 | Kitagawa et al. | 128/788 |
| 4,979,948 | 12/1990 | Geddis et al. | 128/401 X |
| 5,084,044 | 1/1992 | Quint | 128/401 X |

FOREIGN PATENT DOCUMENTS

| 0115420 | 8/1984 | European Pat. Off. . |  |
|---|---|---|---|
| 8527331 | 1/1983 | Fed. Rep. of Germany . |  |
| 57824 | 9/1953 | France | 128/788 |
| 219094 | 8/1968 | U.S.S.R. | 128/788 |
| WO87/01276 | 3/1987 | World Int. Prop. O. . |  |

Primary Examiner—Lee S. Cohen
Attorney, Agent, or Firm—Jacobson, Price, Holman & Stern

[57] ABSTRACT

Apparatus for applying electromagnetic radiation to the pelvic cavity is described, which comprises a first electrode (12) which is inserted into the pelvic cavity (10) in use. A second electrode (14) is also provided and an electromagnetic generating cicuit (1, 2, 6, 9) is coupled to each electrode (12, 14). The frequency generated by the generating circuit (1, 2, 6, 9) in use is emitted by one of the electrodes (12) and received at the other electrode (14) so that the temperature of the cells adjacent to the first electrode (12) is increased above the normal cell temperature. The apparatus is particularly useful for exposing the endometrium to histotoxic temperature and to thus achieve endometrial destruction. Typically, the electromagnetic radiation is radio frequency radiation which is preferably in the range of 500 kHz to 500 MHz. The end (22) of the first electrode (12) may be curved in order to allow access to the cornua regions of the uterine cavity and to improve endometrial contact.

5 Claims, 7 Drawing Sheets

Fig.1

_Fig. 3_

_Fig. 4_

_Fig. 5_

_Fig. 6A_

_Fig. 6B_

_FIG. 7_

_FIG. 8_

ELECTROMAGNETIC ENERGY GENERATION METHOD

The invention relates to apparatus for applying electromagnetic energy to a portion of the body of a patient and, in particular, to the uterine cavity in females.

BACKGROUND OF THE INVENTION

Approximately 1 in 5 gynaecological out-patient referrals are for heavy periods of menorrhagia. The definition of menorrhagia is heavy menstrual loss in the absence of any organic pathology. This condition affects many thousands of women in the UK annually, and the usual course of action is to treat these women is either to use drugs (whose effects are temporary and are very expensive,) or to perform a hysterectomy. Abdominal hysterectomy is the single most commonly performed abdominal surgical procedure in the UK. However, the operation is associated with a definite mortality rate (between b 0.01 and 0.03%) and moreover there is a significant morbidity associated with this operation both in terms of hospital stay (7-10 days), and more importantly, specific complications. In particular, the urinary tract is susceptible to damage by surgical intervention and this has been estimated as occurring at a rate of between 0.5% and 1% in one series of hysterectomies.

Whilst hysterectomy has been the most commonly performed abdominal operation in the UK, 90% of uteri removed because of excessive menstrual loss are histologically and morphologically normal.

The cost of hysterectomising women with menorrhagia is enormous both in terms of operating time, convalescence in hospitals (approximate 7-10 days), and morbidity associated with the operation for up to one year afterwards.

Several attempts have been made over the last 40 years to inactivate the endometrium from which the heavy menstrual loss originates without actually removing the uterus. There are two commonly employed methods at the present time in which there has been enormous interest. The first is the use of the neodymium yttrium aluminium garnet (Nd-YAG) laser system which is hysteroscopically directed at the endometrium and is used to vaporise the endometrium. The second is the hystero-resectoscope which is a modified diathermy loop device similar to a urological resectoscope, where the endometrium is excised, again under direct vision.

Although these two methods of treatment would appear to be effective no one has yet demonstrated conclusive results. Moreover both operations require a highly skilled operative hysteroscopist and both take a considerable amount of time to perform, approximately one hour.

Most importantly of all, both procedures require irrigation of the endometrium cavity with a non-conductive solution such as glycine. Once venules in the endometrium and myometrium are breached, glycine which is highly toxic intravasates, and deaths have been reported due to this.

SUMMARY OF THE INVENTION

In accordance with an aspect of the present invention, apparatus for applying electromagnetic energy to a portion of the body of a patient comprises a first electrode adapted to be inserted into the body of the patient adjacent to the portion of the body in use and an electromagnetic energy generating means coupled to the electrode; and wherein the first electrode is adapted to radiate electromagnetic energy generated by the generating means in use to increase the temperature of cells adjacent to the first electrode above the normal cell temperature.

In accordance with another aspect of the present invention, a method of causing localised heating in a patient comprises inserting a first electrode into the body of a patient adjacent to the portion of the body to be heated, generating electromagnetic energy and coupling said electromagnetic energy to said first electrode so that said first electrode radiates said electromagnetic energy into the portion of the body to be heated to increase the temperature of cells adjacent to said first electrode above the normal cell temperature.

The invention enables the endometrium to be exposed to histotoxic temperatures and thus achieve endometrial destruction. This avoids drawbacks associated with performing a hysterectomy operation and also avoids the drawbacks of using an Nd-YAG laser system to vaporise the endometrium or using a hystero-resectoscope.

Typically, the electromagnetic energy is radio frequency electromagnetic energy. However, it is possible that other frequencies could be used, such as microwave energy.

Preferably, the apparatus further comprises a second electrode so that the energy radiated by the first electrode is received by the second electrode.

Preferably, the second electrode is external and typically is a conductive belt which is insulated and is placed around the patient's abdomen.

In the preferred embodiment, the first electrode is inserted into the uterine cavity.

Typically, the radio frequency generated by the generating means is substantially in the range from 500 kHz to 500 MHz and in the preferred embodiment, a frequency of substantially 27.12 MHz is used.

Preferably, the generating means is an electrical circuit which typically comprises a tuning circuit which enables the circuit to resonate. Typically, the power of the electromagnetic radiation absorbed by a patient can be varied and is typically, of substantially 200 Watts to substantially 1000 Watts for radio frequencies. Preferably, the first electrode is cylindrical and in the preferred embodiment has a diameter of substantially 10 mm, although diameters up to substantially 12 mm could also be used.

Typically, a section of the first electrode which is inserted into the uterine cavity is curved in order to allow access to the cornua regions of the uterine cavity and to improve endometrial contact.

Preferably, the first electrode also incorporates a handle which may enable the section of the probe which is inserted into the uterus to be rotated relative to the handle.

Typically, suction means is also provided to draw the interior walls of the uterine cavity onto the surface of the first electrode. Preferably, the suction means is provided by apertures in the surface of the section of the first electrode which is inserted into the uterine cavity so that suction can be applied through the interior of the first electrode.

Preferably, there is also a temperature sensor located in the portion of the first electrode inserted into the uterine cavity in order to monitor the temperature within the uterine cavity and the temperature sensor could be a thermistor. Typically, the temperature sensor is isolated from a temperature monitor when radio frequency radiation is being generated by an isolation and is connected to the temperature monitor when radio frequency radiation is not being generated. Typically, the isolation means may comprise a number of reed switches which could be activated by air switches connected to a compressor.

A vaginal speculum comprises a hollow body having a leading end, and the end being adapted to co-operate with the anterior fornix of a subject.

Preferably, only a portion of the leading end is adapted to co-operate with the anterior fornix and the remainder of the leading end is at an angle to the direction of insertion of the speculum for each insertion of the speculum into the vagina.

Typically, the external surface of the speculum has means to help prevent expulsion of the speculum by the vagina, and preferably the expulsion prevention means comprises a textured surface on the external surface. Typically, the textured surface comprises circumferential ribbing.

Typically, the speculum has an outside diameter of substantially 40 mm to 50 mm, and is preferably substantially 44 mm. Preferably, the inside diameter of the speculum is substantially 30 mm to 40 mm and is preferably substantially 40 mm.

Guide means may also be provided to aid the location of an instrument within the speculum. Preferably the guide means is resilient and is movable relative to the speculum.

Where the speculum is for use with the apparatus for applying electromagnetic radiation then the speculum is preferably manufactured from an insulating material, such as a plastic and the guide is also preferably manufactured from an insulating material which may also be plastic.

Apparatus for isolating a portion of an electrical circuit form the remainder of the circuit comprises a switch located between the portion and the remainder of the circuit and switching means to switch the switch, wherein the switching means is operated by a fluid.

Preferably, the switch is a reed relay switch and the switching means may include a magnetic and movement of the magnet switches the switch.

Typically, the switching means is operated by compression and decompression of the fluid, and, for example, compression of the fluid could cause the switching means to close the switch and decompression of the fluid could cause the switching means to open the switch. However, the switching means could also be operated by fluid flow.

Where the switching means is operated by compression and decompression of the fluid, the switching means preferably comprises a fluid operated diaphragm switch. However, a fluid operated piston could also be used.

Typically, the fluid could be compressed air. However, other gases and liquids could also be used.

Preferably, the first electrode includes a temperature sensor which is connected to a temperature monitor remote from the first electrode and, typically, the isolating apparatus isolates the temperature sensor from the temperature monitor. This helps to prevent electromagnetic radiation emitted by the first electrode from damaging the temperature sensor and/or the temperature monitor.

Typically, there is more than one switch so that the electrical connection between the temperature sensor and the temperature monitor can be broken in a number of positions to isolate the temperature sensor from the temperature monitor, and to prevent the electromagnetic radiation being conducted by the electrical connection to the temperature monitor.

BRIEF DESCRIPTION OF THE DRAWINGS

An example of apparatus for applying electromagnetic radiation to the pelvic cavity will now be described with reference to the accompanying drawing, in which.

DESCRIPTION OF PREFERRED EMBODIMENTS

Figure 1:
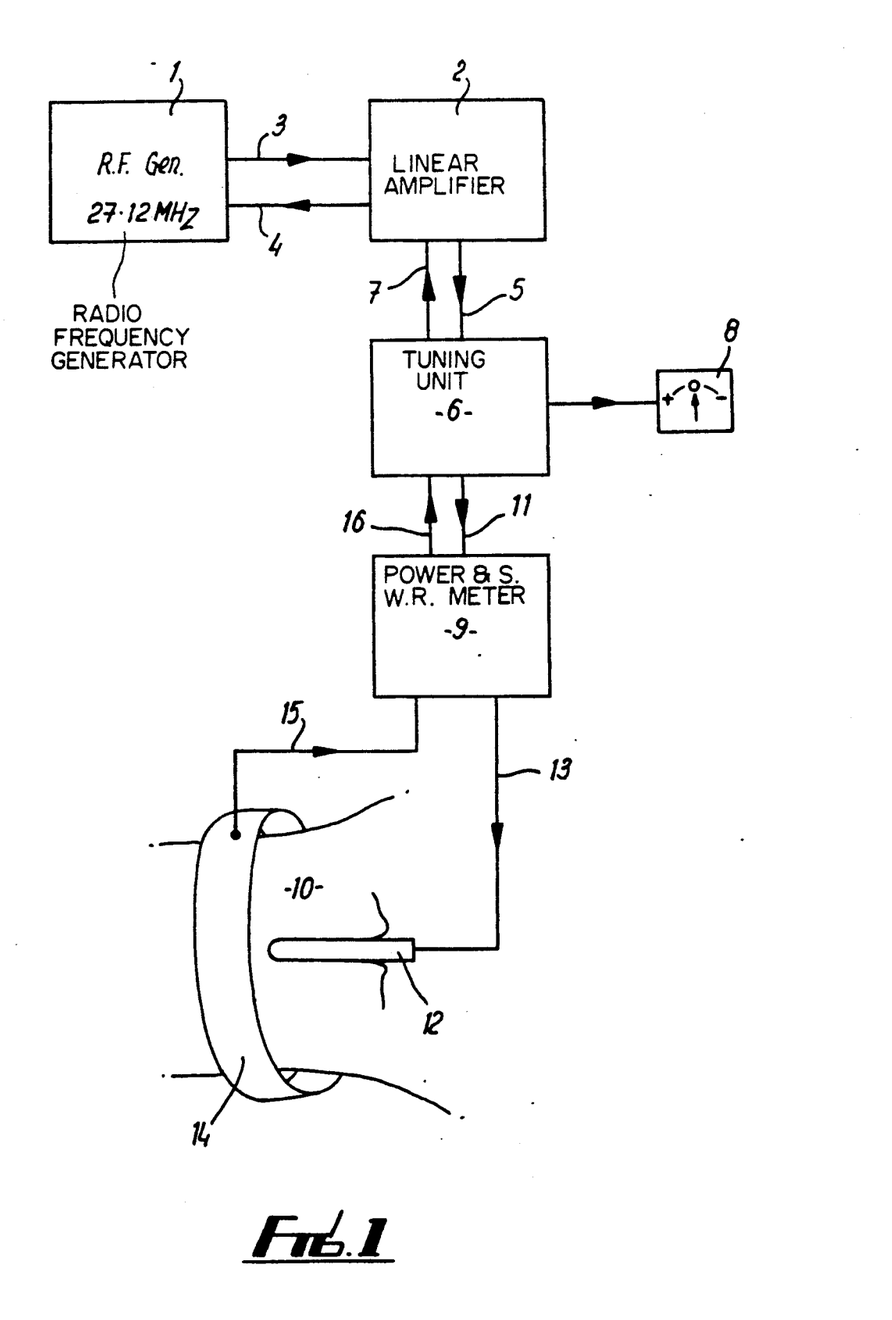
FIG. 1 is a schematic diagram of a first example the apparatus in use with radio frequency electromagnetic radiation.

FIG. 1 shows a radio frequency generator 1 which emits radio frequency electromagnetic radiation at a frequency of 27.12 MHz. A frequency of 27.12 MHz is chosen as it is a standard medical frequency. However, any radio frequency in the range 500 kHz to 500 MHz could be used. Below 500 kHz the flow of electricity is not capacitative and hence the polarisation of particles does not flip between opposite directions as the current alternates and this is essential for heat production. Above 500 MHz the penetration into surrounding tissue is insufficient due to a very rapid reduction in heat production as distance increases.

The radio frequency generator 1 is connected to a linear amplifier 2 via two lines 3, 4. The line 3 transmits the output from the radio frequency generator 1 to the linear amplifier 2 and the line 4 provides a return path from the linear amplifier 2 to the radio frequency generator 1. The output power of the radio frequency generator 1 is approximately 70 Watts and the linear amplifier amplifies this to produce an output power on line 5 of approximately 1 kW. The line 5 transmits the 1 kW of radio frequency at 27.12 MHz from the linear amplifier 2 to a tuning unit 6. The line 7 provides a return path from the tuning unit 6 to the linear amplifier 2.

The tuning unit 6 is tuned to make the circuit resonate and to match the impedance of a patient 10 to the impedance of the system. This is accomplished by use of a meter 8 and when the circuit is resonating there is a zero deflection on the meter 8. The circuit is tuned using the tuning unit 6 in order to ensure that a minimum excess power remains in the circuit and that a maximum amount of power is deposited in the patient 10.

Figure 7:
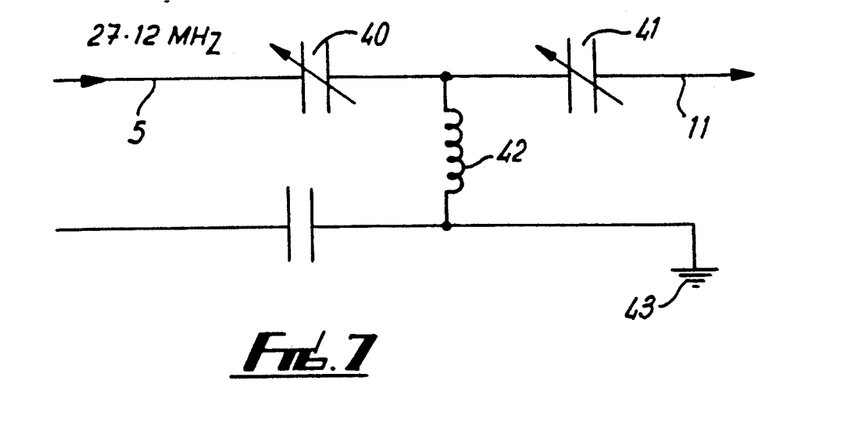
FIG. 7 is a schematic circuit diagram of a first circuit for use in a tuning unit shown in FIG. 1.
Figure 8:
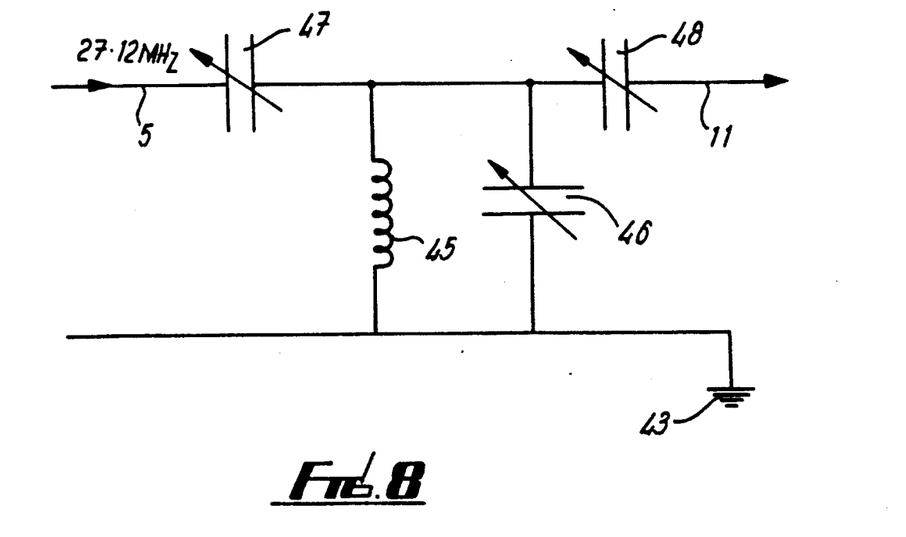
FIG. 8 is a schematic circuit diagram of a second circuit for use in the tuning unit shown in FIG. 1.

FIGS. 7 and 8 show two examples of electrical circuits suitable for use in the tuning unit 6. FIG. 7 shows a circuit which takes the 27.12 MHz signal on the line 5 from the linear amplifier 2 and passes the signal through variable capacitors 40, 41 and outputs the 27.12 MHz signal on the line 11 to the power and SWR meter 9. There is also an inductor 42 which links the 27.12 MHz signal to an earth potential 43. The impedance of the inductor 42 is chosen to match the impedance of the patient 10 and typically the impedance of the patient 10 is about 1000 Ohms.

In order to match the impedance of the patient 10 to the impedance of the system. The variable capacitor 40 is tuned sot hat the combined impedance of the variable capacitor 40 and the inductor 42 matches the radio frequency supply load and typically this is of the order 100 Ohms. The other variable capacitor 41 is then tuned so that the impedance of the patient 10 matches the impedance of the tuning unit 6.

As the wavelength of the radio frequency radiation is in the order of a few meters, standing waves tend to build up in the cable 13 connecting the circuits to the probe 12. It is necessary to obtain a node at the metal end section 22 of the probe 12 in order for the apparatus to be effective. Hence, the inductor 42 also compensates for the length of cable 13 connecting the system to the probe 12.

FIG. 8 shows a circuit having an inductor 45 and a variable capacitor 46 in parallel with each other and with the patient 10 and two variable capacitors 47, 48 which are in series with each other and with the patient 10. As with the circuit shown in FIG. 7 the inductor 45 compensates for the length of the cable connecting the system to the probe 12 and the variable capacitor 47 is for tuning the impedance of the circuit shown in FIG. 8 to the load of the radio frequency generator. The variable capacitors 46, 48 tune the impedance of the patient to the impedance of the circuit. In the circuit shown in FIG. 8 the capacitors 46, 48 are dual variable capacitors so that if the capacitance of the capacitor 48 is changed the capacitance of the capacitor 46 is correspondingly changed. This has the advantage over the circuit shown in FIG. 7 by giving the system a more flexible calibration range but still enabling a fixed valve inductor to be used. As in FIG. 7 the variable capacitors 46, 48 compensate for the differences in impedance between the system and the patient.

It is possible that the variable capacitors 40, 41, 46, 47 and 48 could be replaced by fixed capacitances, however, this would reduce the flexibility of the system.

The output from the tuning unit 6 is transmitted to a power and standing wave ratio (SWR) meter 9 by the line 11 before being supplied to the probe 12 via the line 13. The power and SWR meter 9 enables an operator of the apparatus to monitor the power being deposited in the patient 10.

The probe 12 emits the radio frequency electromagnetic radiation which is then detected by a return electrode in the form of a conductive belt 14 which may be a metal mesh which is insulated and completes the circuit via lines 15 and 16 and the power and SWR meter 9 to provide a return path to the radio frequency generator 1. The cable forming the line 15 may be soldered on to the metal mesh of the belt 14 or may be crimped on to the mesh.

In use, the probe 12 which is a conductive metal probe is inserted into the pelvic cavity. In this example the apparatus is designed to destroy the endometrium in the uterus of the female patient 10. Hence, in this example the probe 12 is inserted into the uterus of the patient 10, as shown in FIG. 1. The belt 14 which acts as the return electrode is placed around the patient's abdomen. The apparatus is then tuned using the tuning unit 6 and the meter 8 to the resonant series circuit formed by the probe 12 and the belt 14.

It is known that if the mammalian cells are heated to 43° C. they survive for an hour and that this thermotolerance time is halved for every degree rise in temperature. Hence, at a temperature of 47° C. mammalian cells survive for approximately 4 minutes.

The effect of radio frequency electromagnetic radiation on biological tissue to produce a heating effect. An electric field is set up around the probe 12 in the uterine cavity and tissue lying within that field is heated. In the case of the apparatus described here the tissue is heated to a depth of approximately 5 mm.

When the apparatus is energised the result is that the whole pelvic cavity is heated but due to the geometry of the apparatus heat is concentrated almost exclusively at the endometrium which is in contact with the surface of the probe 12. Temperatures achieved at the endometrium are in the range 46° C. to 55° C.

Hence, it is possible to heat the entirety of the endometrium to histotoxic temperatures and achieve endometrial destruction which is known as total simultaneous endometrial ablation (TSEA).

With the apparatus shown in FIG. 1 the magnitude of the power deposited in the patient 10 is approximately 550 watts if the cable which forms the line 13 is about 4.8 m long, and this is the power absorbed by the patient 10 as heat. However, if the length of the cable is reduced to about 2.08 m the power may be reduced to about 300 W. The apparatus could incorporate a variable power output so hat powers in the range 200 Watts to 1000 Watts could be absorbed. As the blood supply to the uterus is very large the blood in the uterus acts as a heat sink and so heating of the surrounding tissue is prevented. The probe 12 has a diameter of approximately 10 mm to 12 mm. If the diameter is substantially less than this then the uterus is not fully extended and folds and recesses remain in the wall. These folds can result in under treatment of tissue hidden by the folds. In addition, if the diameter is less than 10 mm the surface of the probe 12 becomes much hotter and consequently provides less penetration into the surrounding tissue. A smaller probe would also mean a sharper end to the probe which would create a hot spot and this is avoided in a 10 mm diameter probe using the powers described above.

A probe with a diameter greater than 12 mm is not practical as the cervix does not easily dilate to more than 12 mm.

Figure 2:
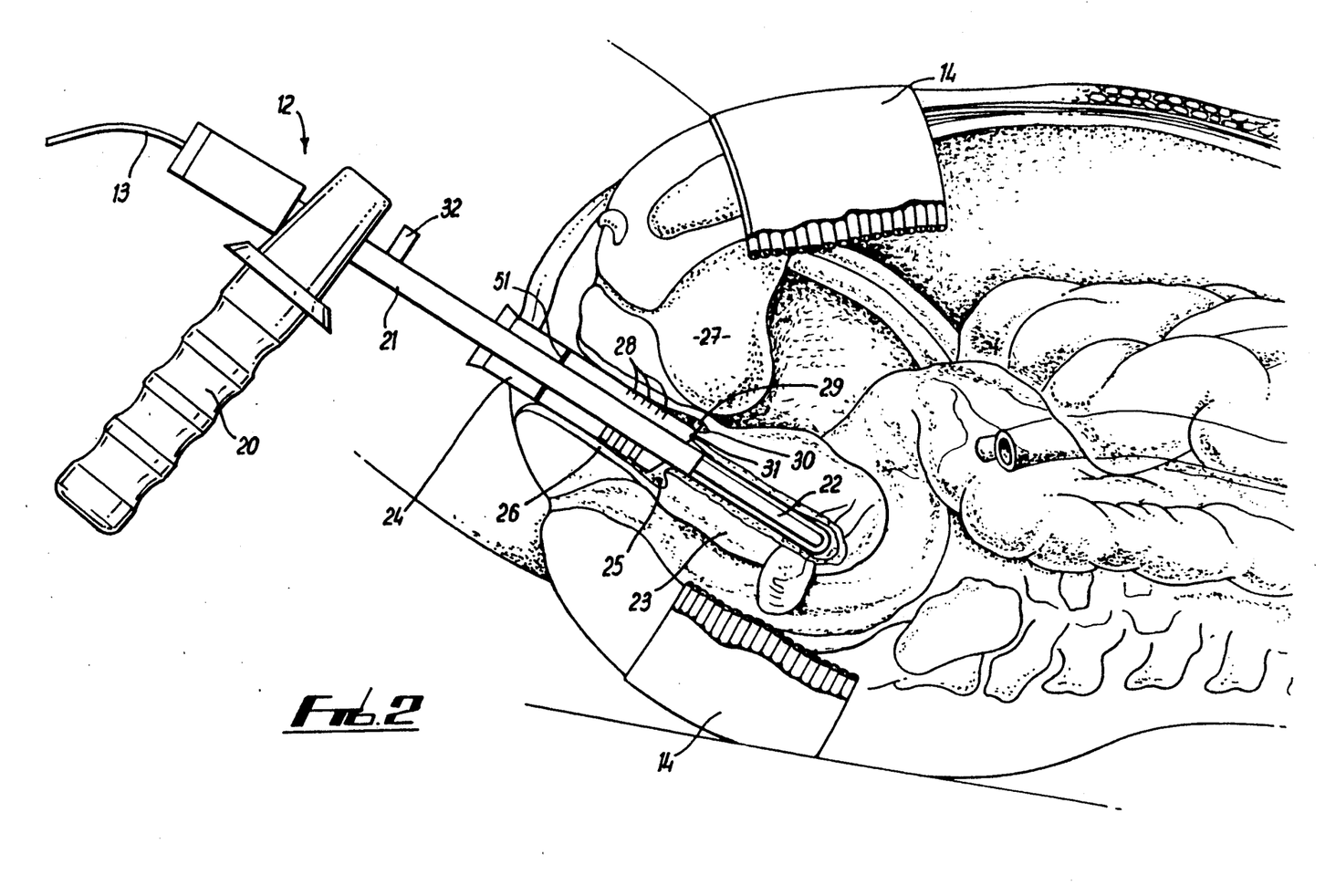
FIG. 2 is a diagram showing the apparatus in use during treatment of a patient.

FIG. 2 shows the apparatus of FIG. 1 being used to treat a patient. As shown in FIG. 2 the probe 12 comprises a handle 20 which is connected to a highly insulating plastic sheath 21, the line 13 is fed through the plastic sheath 21 and makes electrical contact with a metal end section 22 of the probe 12.

The handle 20 is rotatable on the plastic sheath 21 so that if the end section 22 is curved then the end section 22 maybe be positioned in any orientation relative to the inside of the uterus 23.

Also shown in a vaginal speculum 24 which is electrically insulating and is inserted into the vagina 25 of the patient 10 prior to insertion of the probe 12 through the vagina 25 and into the uterus 23. The speculum 24 protects the side walls 26 of the vagina 25 from accidental damage caused by localised heating by the metal end section 22 of the probe 12, which can burn a hole through the vaginal wall 26 into the other organs, such as the bladder 27 if it accidentally touches the vaginal wall 26. As shown in FIG. 2, and in more detail in FIGS. 9A and 9B, the speculum 24 has a number of ribs 28 on it's outside surface 50 in order to prevent expulsion of the speculum 24 by the vagina 25.

Figure 9A:
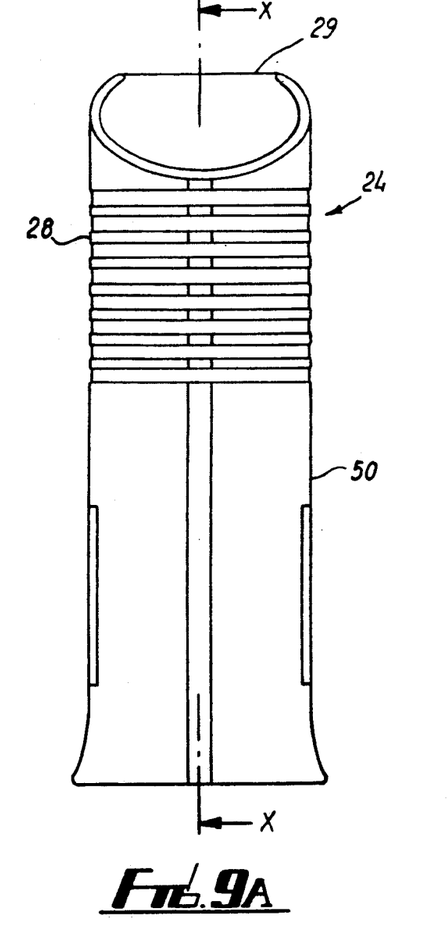
FIG. 9A and 9B show a speculum for use during treatment of the patient as shown in FIG. 2.
Figure 9B:
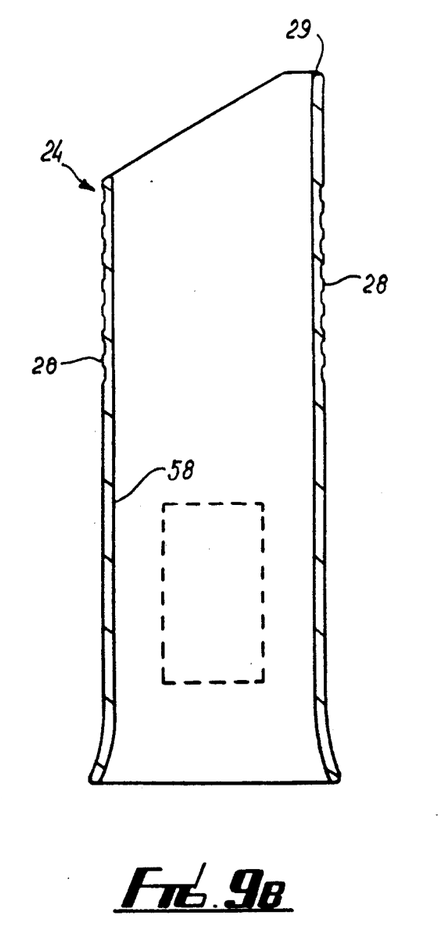

The speculum 24 also has a lip 29 which fits into the anterior fornix 30 on the upper side of the cervix 31 so that the cervix 31 fits within the lip 29 of the speculum 24 and this helps prevent the metal end section 22 of the probe 12 contacting the vaginal wall 25.

In order to help location of the metal end section 22 through the cervix and into the uterus, a guide 51 is provided which may be movable on the plastic sheath 21 and/or within the speculum 24. Two examples of a guide 51 are shown in detail in FIGS. 10 and 11.

Figure 10:
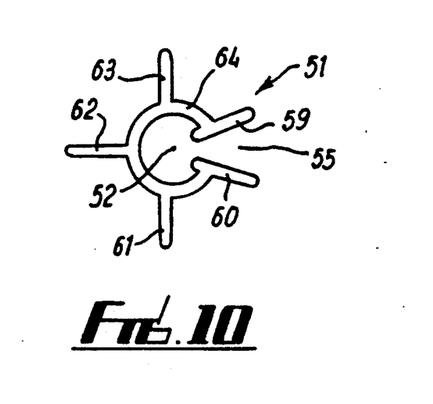
FIG. 10 shows a first example of a guide for use with the speculum shown in FIG. 9.

FIG. 10 shows a guide 51 of moulded plastic which has a central aperture 52 into which the plastic sheath 21 of the probe 12 is located. There are also two side apertures 53, 54, which enables an operator to view the cervix through the guide 51. An entrance 55 is also provided to enable the probe 12 to be inserted into the central aperture 52. Arcuate portion 56, 57 fit against the inside surface 58 of the speculum 24 and are resilient so that the guide 51 is retained in position in the speculum 24.

Figure 11:
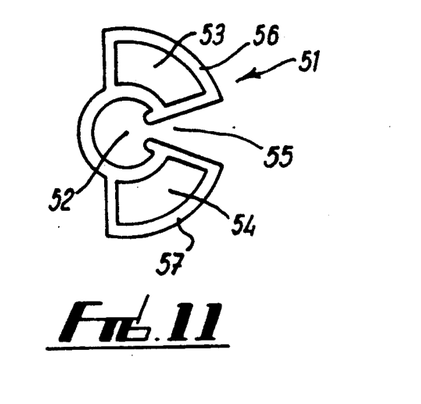
FIG. 11 shows a second example of a guide for use with the speculum shown in FIG. 9.

FIG. 11 shows a guide 51 which has five radially extending arm portions 59, 60, 61, 62 and 63. One end of each of the arms 59 to 63 are attached to a central section 64 which forms the central aperture 52. The other ends of the arms 59 to 63 abut against the inside surface 58 of the speculum 24 and are resilient in order to hold the guide in position within the speculum 24. The guide 51 in FIG. 10 also has an entrance 55 through which the probe may be inserted into the central aperture 52.

Attached to the plastic sheath 21 is a lever 42 which enables an operator to easily rotate the orientation of the metal end section 22 relative to the handle 20.

Figure 3:
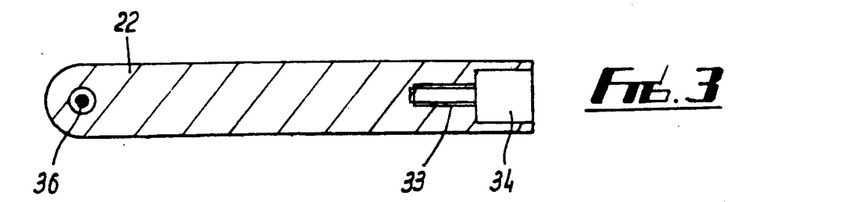
FIG. 3 shows a first example of a probe for use in the apparatus shown in FIGS. 1 and 2.
Figure 4:
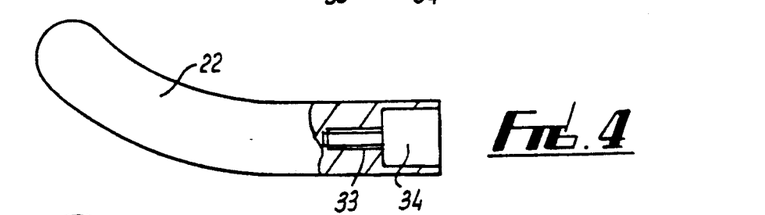
FIG. 4 shows a second example of a probe for use in the apparatus shown in FIGS. 1 and 2.

FIG. 3 shows a first example of the metal end section 22 which is straight. Also shown is a blind bore 33 which makes electrical contact between the metal end section 22 and the conductor carrying the radio frequency signal. There is also a recess 34 into which an end 34 of the plastic sheath 21 fits. FIG. 4 illustrates a second example of a metal end section 22 in which the metal end section 2 is curved to enable the end section 22 to more effectively contact the interior surface of the uterus.

Figure 6A:
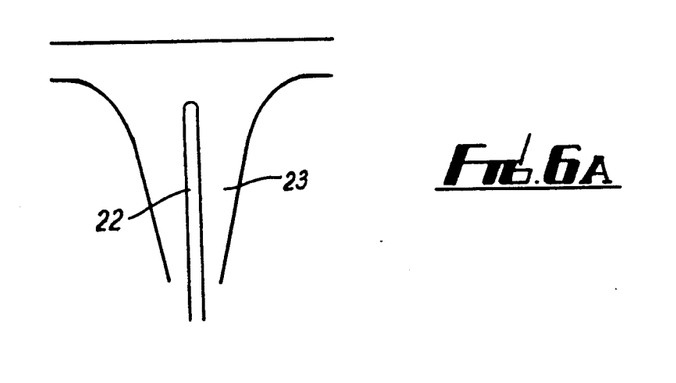
FIGS. 6A and 6B illustrate the probes shown in FIGS. 3 and 4, respectively in use.
Figure 6B:
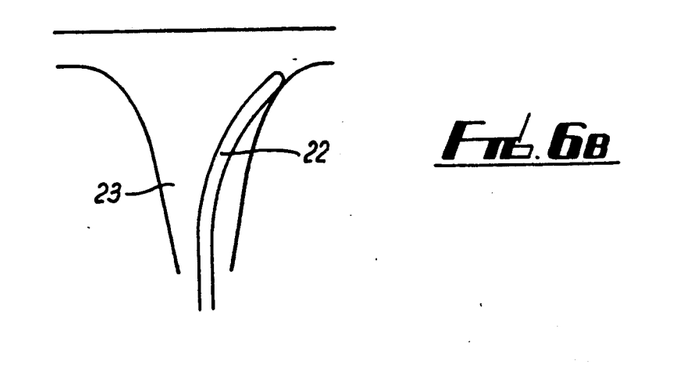

The advantages of the curved end section 22 shown in FIG. 4 over the straight end section 2 shown in FIG. 3 are shown schematically in FIGS. 6A and 6B. FIG. 6A shows that with the straight end section 22 shown in FIG. 3 it is difficult for the end section 2 to effectively contact the interior surfaces of the uterus 23 without moving the probe from side to side within the uterus 23, which could cause damage to the uterus. As shown in FIG. 6B, the curved end section, shown in FIG. 4, enables the end section 22 to effectively contact the interior surfaces of the uterus 23 without the probe 12 having to be moved from side to side.

Figure 5:
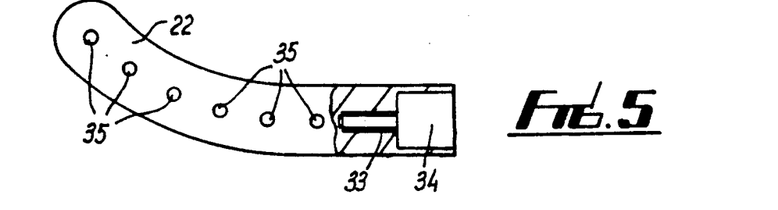
FIG. 5 shows a third example of a probe for use in the apparatus shown in FIGS. 1 and 2.

FIG. 5 shows a metal end section 22 which is curved and which also has a number of apertures 35 in the external surface of the end section 22. This feature enables suction to be applied to the probe 12 so that air is drawn from the uterus 23 through the apertures 35 and through the probe 12 to a suitable vacuum pump attached to the probe 12. The suction applied to the uterus 23 through the probe 12 enables the walls of the uterus to be drawn onto the end section 22 of the probe 12 and this also improves the contact between the walls of the uterus 23 and the surface of the end section 22.

Figure 13:
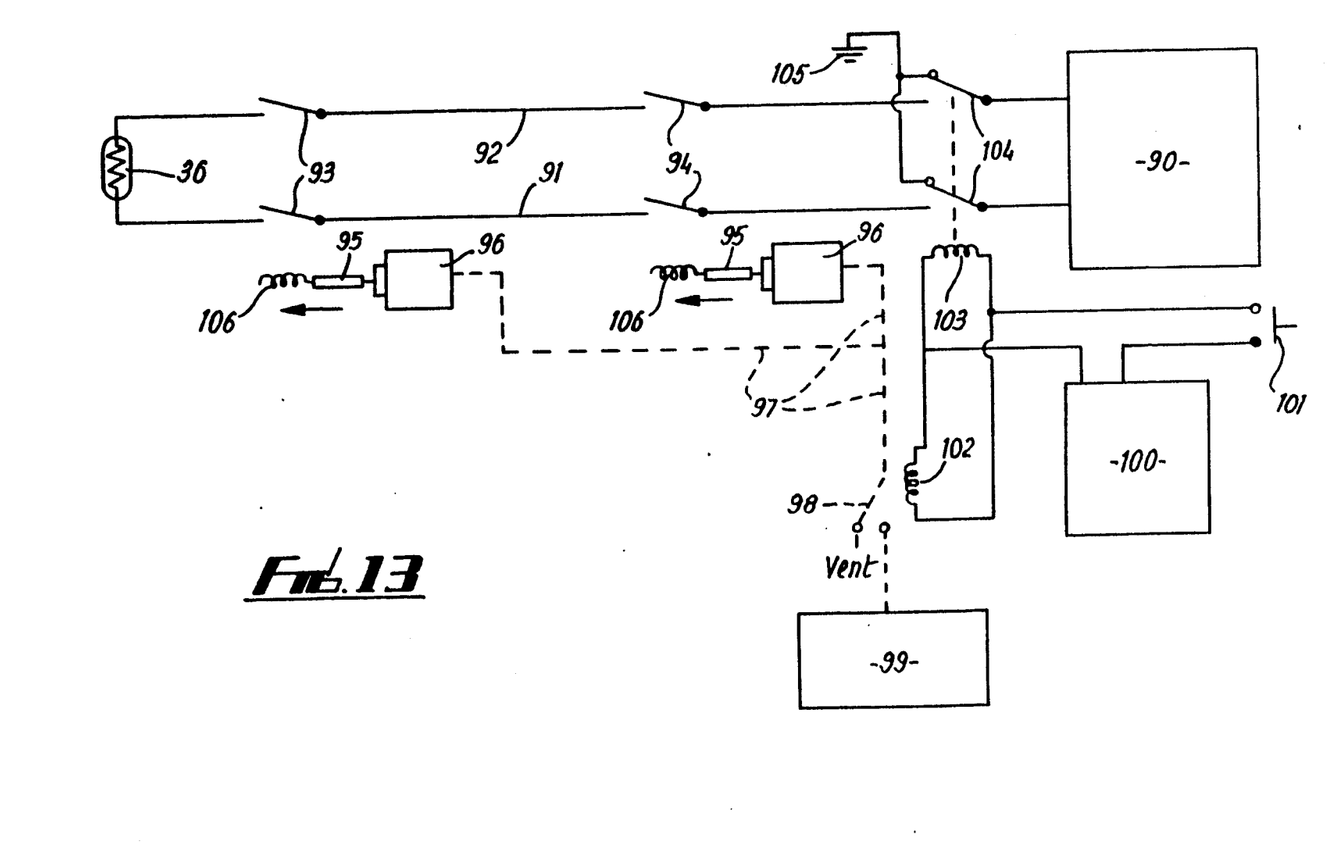
FIG. 13 is a schematic diagram shown a temperature monitoring circuit for use with the apparatus shown in FIGS. 1 and 12.

A thermistor 36 is mounted in the tip of the end section 22 and is connected to an external monitoring circuit 90 as shown in FIG. 13. The thermistor 36 is connected to the monitor 90 via two lines 91, 92. Each line 91, 92 has three reed relay switches 93, 94, 104, and the switches 93, 94, 104 are high voltage isolation reed switches which have a blocking isolation of about 3 kV. The switches 93, 94 are operated by movable magnets 95 which are moved by diaphragm air operated switches 96 and the air switches 96 are connected via air lines 97 and a valve 98 to a compressor 99.

A DC power supply 100 is connected to a switch 101 and two coils 102, 103. The coil 102 is adjacent to the valve 98 and the coil 103 is adjacent to the pair of reed switches 104 in the lines 91, 92. When the switch 101 is open no current from the supply 100 flows through the coils 102, 103 and so the valve 98 is open to the atmosphere and the switches 104 connect the temperature monitor 90 to an earth potential 105. When the switch 101 is closed current from the DC supply 100 flows through the coils 102, 103 and the current flowing through the coils 102, 103 generates a magnetic field in the vicinity of the coils 102, 103. This magnetic field actuates the valve 98 causing the valve 98 to close. This in turn directs compressed air from the compressor 99 through the lines 97 to the air switches 96. The compressed air activates the air switches 96 which move the magnets 95 against the action of springs 106 and the movement of the magnets 95 cause the reed switches 93, 94 to close. At the same time the magnetic field generated by the coil 103 causes the reed switches 104 to switch to connect the monitor 90 to the lines 91, 92. Hence, the monitor 90 is connected to the thermistor 36 via lines 91, 92 and the switches 93, 94, 104.

Simultaneously, with the closing of the switch 101, the radio frequency generator 1 is switched off by a switch (not shown). This prevents the radio frequency generated by the generator 1 from interfering with the monitoring of the temperature of the thermistor 36 by the monitor 90 and also prevents the power from the radio frequency becoming dissipated into the temperature monitoring circuit and burning out the thermistor 36 and/or the monitor 90. In addition, the air lines 97 and the switches 96 are all manufactured from non-metallic components to prevent radio frequency oscillation being generated in their components.

After the temperature has been monitored by the circuit 90, the switch 101 is opened which causes the switches 104 to re-connect the circuit 20 to the earth potential 105 and the value 98 to open. This allows the air pressure in the air switches 96 and the lines 97 to drop and so the switches 96 are de-activated and the magnets 95 are returned to their original position by the biasing action of the springs 106 which causes the reed switches 93, 94 to open. At the same time the radio frequency generator 1 is switched on again and the ablation of the endometrium continues.

Typically, the temperature sampling procedures as described above occurs at pre-determined intervals so that the temperature at the probe end is regularly monitored and displayed on a display (not shown) which is visible to an operator.

Figure 12:
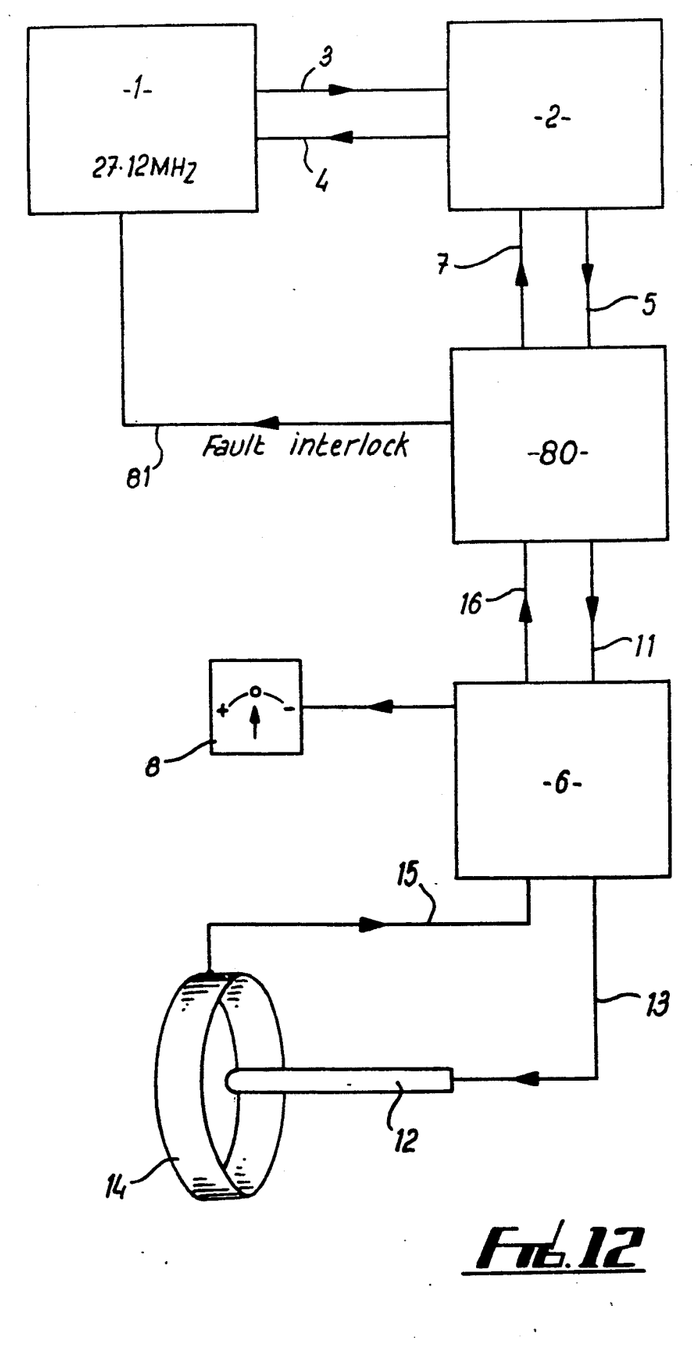
FIG. 12 is a schematic diagram of a second example of the apparatus.

FIG. 12 shows a second example of apparatus for achieving TSEA. The apparatus is the same as the apparatus shown in FIG. 1, except that the power and SWA meter 9 is not used and the tuning unit 6 is connected directly to the lines 13, 15. Instead of the power and SWR meter 9, a forward power measurement and normalised reflected power indication unit 80 is located between the linear amplifier 2 and the tuning unit 6. There is also a fault interlock line 81 which connects the indication unit 80 directly to the radio frequency generator 1.

The indication unit 80 monitors the tuning unit 6 and the status of the tuning unit 6 is related to the power being dissipated in the patient 10. Hence, the indicator 80 indirectly monitors the patient 10. If the indicator 80 detects that the reflected power rises above a pre-determined level then this indicates that there is a fault in the apparatus and the indicator 80 sends a signal on the line 81 to cut off the radio frequency generator 1.

Treatment of menorrhagia using the apparatus described above and shown in FIG. 1 to achieve TSEA is radically different from the laser and diathermy loop methods. In these methods only small areas of the endometrium can be treated at one time and hence the radio frequency treatment described above is a much faster method of treatment. Therefore this treatment is in the long term significantly cheaper than other known methods of treatment such as using lasers or a diathermy loop or by performing a hysterectomy operation. Modifications and improvements may be incorporated without departing from the scope of the invention.

We claim:

1. A method of causing endometrial destruction in a patient, the method comprising:
    inserting a first electrode into a uterine cavity of the patient;
    generating radio-frequency electromagnetic energy;
    coupling said radio-frequency electromagnetic energy to said first electrode; and
    emitting said radio-frequency electromagnetic energy from said first electrode
    wherein the method includes the step of extending the uterine cavity by said first electrode when said first electrode is inserted into the uterine cavity so that a majority of the inside surface of the uterine cavity contacts said first electrode; and
    wherein the uterine cavity has an endometrium and said first electrode radiates said radio-frequency electromagnetic energy into the uterine cavity and increases the temperature of cells of the endometrium adjacent to said first electrode above the normal cell temperature to destroy the cells of the endometrium.

2. A method according to claim 1, further comprising arranging a second electrode so that the endometrium is located between said first electrode and said second electrode.

3. A method according to claim 2, wherein said second electrode is external to the patient.

4. A method according to claim 1, wherein said radio-frequency electromagnetic energy is substantially in the range from 500 kHz to 500 MHz.

5. A method according to claim 1, wherein the temperature of the cells of the endometrium is increased to between 46° C. and 55° C.

* * * * *